United States Patent [19]

Kraus

[11] Patent Number: 4,851,433

[45] Date of Patent: Jul. 25, 1989

[54] THERAPEUTIC AGENTS CONTAINING TAMOXIFEN AND SALTS THEREOF

[75] Inventor: Hans A. Kraus, Waiblingen-Neustadt, Fed. Rep. of Germany

[73] Assignee: Imperial Chemical Industries plc, London, England

[21] Appl. No.: 15,034

[22] Filed: Feb. 17, 1987

[30] Foreign Application Priority Data

Feb. 24, 1986 [GB] United Kingdom ............... 8604528

[51] Int. Cl.⁴ .......................................... A61K 31/135
[52] U.S. Cl. ................................... 514/648; 514/863
[58] Field of Search ............................... 514/648, 863

[56] References Cited

U.S. PATENT DOCUMENTS 4,061,733 12/1977 Gunjikar ............................ 514/648
4,536,516 8/1985 Harper et al. ...................... 514/648
4,656,187 4/1987 Black et al. ........................ 514/648

FOREIGN PATENT DOCUMENTS 85196517 8/1985 France .

*Primary Examiner*—Leonard Schenkman
*Attorney, Agent, or Firm*—Cushman, Darby & Cushman

[57] ABSTRACT

The invention concerns a new therapeutic agent for use in treating psoriasis, new compositions of the therapeutic agent for topical administration and a new method of treating psoriasis.

3 Claims, No Drawings

THERAPEUTIC AGENTS CONTAINING TAMOXIFEN AND SALTS THEREOF

This invention relates to a therapeutic agents for use in a new method of medical treatment and, more particularly, it relates to an agent for use in a new method for the treatment of psoriasis and to topical formulations of said agent.

Psoriasis is a common chronic inflammatory disease of the skin and in some cases, also the joints, which affects virtually all ages and which is difficult to treat successfully. The aetiology of psoriasis is largely unknown and the objective of most treatment is to suppress the abnormally rapid skin cell turnover process rather than to effect a cure. Topical treatments such as dithranol and coal tar derivatives, with or without UV irradiation, have some effect in controling mild to moderate psoriasis, but the more severe cases require systemic treatment with cytotoxic agents such as methotrexate which have overt adverse side effects. Present treatments of psoriasis have been reviewed by R.H. Champion (*British Medical Journal*, 1986; 292, 1693). There is thus a need for a new therapeutic agent which is capable of controlling psoriasis without the production of unwanted side-effects.

It has now been found that administration of tamoxifen (as its citrate salt) results in the remission of psoriasis of long standing without any overt side-effects and this is the basis of the invention.

According to the present invention there is provided a method for the treatment of psoriasis affecting a warm-blooded animal which comprises the administration to said animal of an effective amount of tamoxifen or a pharmaceutically acceptable acid-addition salt thereof.

According to a further feature of the invention there is provided the use of tamoxifen, or of a pharmaceutically acceptable acid addition salt thereof, for the treatment of psoriasis affecting a warm-blooded animal such as man.

According to a yet further feature of the invention there is provided the use of tamoxifen, or of a pharmaceutically acceptable acid-addition salt thereof, for the manufacture of a novel medicament for the treatment of psoriasis affecting a warm-blooded animal such as man.

The chemical compound tamoxifen [(Z)-2-[p-(1,2-diphenylbut-1-enyl)phyenoxy]ethyldimethylamine]is known to be especially useful in the treatment of hormone-dependent tumours, and especially in the treatment of breast cancer in women. Comprehensive reviews of its clinical usage are available, for example by Furr and Jordan in "Pharmacology and Therapeutics", 1984, Volume 25, pages 127–205. Tamoxifen also has utility in treating male infertility (Furr and Jordan, above, Section 8.3.1.2, page 185).

A suitable pharmaceutically acceptable acid-addition salt is, for example, the hydrochloride, hydrobromide, citrate or D-gluconate salt. The last salt is particularly suitable for the production of topical formulations of tamoxifen.

It is to be understood that "warm blooded animal" includes both male and female humans.

The tamoxifen or an acid-addition salt thereof (hereafter referred to as "the therapeutic agent") may be administered, for example orally or topically for the relief of psoriasis, and may be used in a conventional oral or topical formulation.

Topical formulations of the therapeutic agent for use in the treatment of psoriasis are novel and are provided as a further feature of the invention and comprise tamoxifen or a pharmaceutically acceptabe acid-addition salt thereof (especially a generally water-soluble salt such as the D-gluconate) together with one or more dermatologically acceptable excipients.

A suitable oral formulation, is for example, a tablet or capsule, preferably a tablet containing, for example, 10, 20, 30 or 40 mg, of therapeutic agent. In general, it will be administered at a dose in the range 20 to 80 mg. per day, either as a single dose or as divided doses.

A suitable topical formulation is, for example, an ointment, cream or lotion containing up to 10% by weight of the therapeutic agent and typically in the range, for example 0.1 to 5% by weight. This will normally be applied to the skin of the patient (either to the unaffected or the psoriatic area) once or twice per day. Topical formulations may be obtained by conventional procedures and using dermatologically acceptable excipients, well known in the art.

Examples of dermatologically suitable excipients include those well known in the art of pharmacy for the production of topical formulation, such as arachis oil, non-volatile fatty alcohols, acids and/or esters (e.g. cetostearyl alcohol, cetyl alcohol, stearyl alcohol, stearic acid or cetyl esters wax); volatile alcoholic compounds [e.g. lower alkanols such as ethanol or isopropanol]; glycols and glycol ethers (e.g. propylene glycol or ethyl digol); glycerol and glycerol ethers; emulsifying gents (e.g. sorbitan stearate, sorbitan trioleate, polysorbate 60 or a mixture of polyoxyethylated oleyl or cetyl alcohol); preservatives (e.g. (1–4C)alkyl hydroxybenzoates such as methyl or propyl hydroxybenzoates); and non-volatile hydrocarbons such as soft paraffin or liquid paraffin. Examples of suitable formulations are provided in the accompanying Examples.

An agent to improve penetration through the skin, for example dimethyl sulphoxide, N-methyl-2-pyrrolidinone or 1-dodecylazacycloheptan-2-one, may also conveniently be present in a topical formulation.

A particular ointment formulation may be prepared, for example, by dispersing the therapeutic agent as defined above in a suitable organic diluent, for example soft paraffin, optionally in the presence of an emulsifying and/or thickening agent, for example sorbitan monostearate.

A particular emulsion formulation such as a cream or lotion may be obtained for example, by adding a slurry of tamoxifen free base in ethanol or 2-propanol to an aqueous solution of D-gluconic acid to form tamoxifen gluconate in situ, which mixture is then combined with the required components of the disperse phase.

The topical formulations are conveniently provided for the treatment of psoriasis packaged in dispensers such as deformable tubes containing for example, 5 to 200 g of formulation and such filled dispensers are provided as a further feature of the invention.

One preferred formulation for oral administration contains tamoxifen citrate together with one or more pharmaceutically acceptable diluents or carrier in the form of a tablet containing 10, 20, 30 or 40 mg of active ingredient, for example, such as is commercially available under the ICI trade mark 'Nolvadex' for use in the treatment of breast cancer.

A preferred formulation for topical administration contains tamoxifen D-gluconate together with one or more dermatologically acceptable excipients in the form of an ointment, cream or lotion. In addition, the therapeutic agent may also be administered topically by spray or aerosol.

The invention is illustrated, but not limited, by the following Examples:

EXAMPLE 1

A white male patient, aged about 33 years, had been afflicted with psoriasis for about 10 years, the worst areas affected being the palms of his hands. All previous attempts to treat this condition had failed. The patient was also infertile, and treatment for the infertility was attempted by the oral administration of tamoxifen citrate (available under the trade mark 'Nolvadex' from Imperial Chemical Industries PLC) at a dose of 20 mg twice per day. After 2 months of treatment, all symptoms of the psoriasis disappeared. After a further 3 months, treatment was discontinued and the psoriasis returned 3 weeks later. Treatment with tamoxifen citrate was recommenced and the psoriasis again disappeared, and remained absent as treatment was continued. No untoward effects were observed during the period of treatment.

EXAMPLE 2

Clinical responses to oral treatment with tamoxifen citrate have been observed in a number of additional patients. For example a white male patient, aged about 32 years and afflicted with severe psoriasis for several years, showed a marked reduction in symptoms following administration of tamoxifen citrate orally at 20 mg twice daily. The beneficial effect was lost on withdrawing the therapeutic agent but returned with further treatment. No adverse effects were observed during treatment.

EXAMPLE 3

(Components are given in % w/w unless otherwise stated.)

This example describes a number of typical cream formulations for topical use and which contain tamoxifen as its D-gluconate salt.

For each formulation, the tamoxifen D-gluconate salt may be obtained by mixing an ethanolic slurry of tamoxifen as the free base with an aqueous solution of D-gluconic acid, obtained by hydrlysing a 20% w/v solution of D-gluconolactone in water by heating at 70° C. for 15 to 30 minutes. [Note: the minimum volume of ethanol is used and 5 ml of the aqueous D-gluconic acid solution is added per 1 g of tamoxifen free base]. Stirring is then continued until a clear solution is obtained. The required volume of this solution is then added to other excipients to produce the following cream formulations in which "active ingredient" is tamoxifen D-gluconate salt:

| FORMULATION I | |
|---|---|
| Active ingredient | 0.5–2.5 |
| Cetostearyl alcohol | 4.0 |
| Cetyl esters wax (synthetic spermaceti) | 2.0 |
| Arachis oil | 5.0 |
| *'Brij' 72 (steareth 2) | 2.5 |
| **'Brij' 78 (steareth 20) | 1.5 |
| Methyl hydroxybenzoate | 0.15 |
| Propyl hydroxybenzoate | 0.08 |
| Purified water | to 100% |

*polyethylene glycol ether of stearyl alcohol containing an average of 2 oxyethyl groups per molecule ['Brij' is a trade mark].
**polyethylene glycol ether of stearyl alcohol containing an average of 20 oxyethyl groups per molecule.

| FORMULATION II | |
|---|---|
| Active ingredient | 0.5–2.5 |
| Cetostearyl alcohol | 5.0 |
| Cetyl esters wax (synthetic spermaceti) | 3.0 |
| Liquid paraffin | 3.0 |
| Glyceryl stearate SE (Self emulsifying grade) | 3.0 |
| 'Brij' 78 (Steareth 20) | 1.0 |
| Methyl hydroxybenzoate | 0.15 |
| Propyl hydroxybenzoate | 0.08 |
| Butylated hydroxytoluene | 0.05 |
| Purified water | to 100% |

| FORMULATION III | |
|---|---|
| Active ingredient | 0.5–2.5 |
| *'Arlatone' 983S | 4.0 |
| Cetyl alcohol | 2.5 |
| Stearic acid | 1.5 |
| Propylene glycol | 2.0 |
| Glycerin | 2.0 |
| Methyl hydroxbenzoate | 0.15 |
| Propyl hydroxybenzoate | 0.08 |

*Polyethylene glycol ether derivative (containing an average of 5 oxyethyl units per molecule) of glyceryl stearate ['Arlatone' is a trade mark].

| FORMULATION IV | |
|---|---|
| Active ingredient | 0.5–2.5 |
| Cetostearyl alcohol | 1.0 |
| Stearic acid | 1.5 |
| *"Arlamol" E (PPG 15 stearyl ether) | 9.0 |
| 'Brij' 72 (steareth 2) | 3.0 |
| **'Brij' 721 (steareth 21) | 3.0 |
| Propylene glycol | 2.0 |
| Methyl hydroxybenzoate | 4.0 |
| Propyl hydroxybenzoate | 0.15 |
| Purified water | 0.08 |
| | to 100% |

*polypropylene glycol ether of stearyl alcohol containing an average of 15 2-oxy-propyl groups per molecule.
**polyethylene glycol ether of stearyl alcohol containing an average of 21 oxyethyl groups per molecule.
['Arlamol' is a trade mark]

| FORMULATION V | |
|---|---|
| Active ingredient | 0.5–2.5% |
| Cetostearyl alcohol | 5.0 |
| Cetyl esters wax (synthetic spermaceti) | 2.0 |
| 'Span' 60 (sorbitan stearate) | 2.0 |
| 'Tween' 60 (polysorbate 60) | 2.0 |
| Glycerol | 1.0 |
| Methyl hydroxybenzoate | 0.15 |
| Propyl hydroxybenzoate | 0.08 |
| Purified water | to 100% |

['Span' and 'Tween' are trade marks]
NOTES:
(i) The methyl and propyl hydroxybenzoates are present as preservatives and may be replaced by one or more other conventional preservatives.
(ii) The above formulations may optionally contain 0.5 to 5.0% of a penetration enhancer such as dimethyl sulphoxide.
(iii) It will be understood that the above formulations will also contain residual ethanol from the initial preparation of the active ingredient.

EXAMPLE 4

(Components are given in % w/w except where indicated)

This Example illustrates an ointment formulation suitable for topical administration:

| | |
|---|---|
| Active ingredient* | 0.5 |
| Ethyl digol | 5.0 |
| Ethanol 96% B.P. | 3.0 w/v |
| Purified water | 2.0 |
| 'Span' 85 (sorbitan trioleate) | 3.0 |
| White soft paraffin | to 100% |

*Note: the active ingredient may either be tamoxifen D-gluconate (conveniently prepared in situ in the ethanol/ethyl digol mixture) or tamoxifen citrate.

EXAMPLE 5

(Components are given in % w/w)

This Example illustrates a further ointment formulation suitable for topical formulation:

| | |
|---|---|
| Active ingredient* | 0.5–2.5 |
| Light liquid paraffin | 5–10 |
| White soft paraffin | to 100% |

*Note: the active ingredient may be, for example, finely micronised tamoxifen citrate or finely powdered tamoxifen D-gluconate (for example such as may be obtained by freeze-drying an aqueous solution of the salt).

What is claimed is:

1. A method for the treatment of psoriasis in a warm-blooded animal requiring such treatment which comprises administering to said animal an effective amount of therapeutic agent selected from tamoxifen and the pharmaceutically acceptable salts thereof.

2. The method of claim 1 wherein the pharmaceutically acceptable salts are water-soluble salts.

3. The method of claim 1 wherein the therapeutic agent is the D-gluconate salt of tamoxifen.

* * * * *

UNITED STATES PATENT AND TRADEMARK OFFICE
CERTIFICATE OF CORRECTION

PATENT NO. : 4,851,433
DATED : July 25, 1989
INVENTOR(S) : KRAUS, Hans A.

It is certified that error appears in the above-identified patent and that said Letters Patent is hereby corrected as shown below:

On the face of the patent, under -
FOREIGN PATENT DOCUMENTS   Please delete:

"85196517 8/1985 France"

and insert in place of the deletion:

--WO-A-8503228--

Signed and Sealed this

Fourth Day of September, 1990

*Attest:*

HARRY F. MANBECK, JR.

*Attesting Officer*   *Commissioner of Patents and Trademarks*